United States Patent
Herleikson

(10) Patent No.: US 6,560,485 B2
(45) Date of Patent: May 6, 2003

(54) FOUR CONTACT IDENTIFICATION DEFIBRILLATOR ELECTRODE SYSTEM

(75) Inventor: Earl Clark Herleikson, Lebanon, ME (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/817,223

(22) Filed: Mar. 27, 2001

(65) Prior Publication Data

US 2002/0143366 A1 Oct. 3, 2002

(51) Int. Cl.[7] .................................................. A61N 1/37
(52) U.S. Cl. ............................................. 607/27; 607/5
(58) Field of Search ..................... 607/5, 8, 27, 119, 607/142, 152; 600/509, 522

(56) References Cited

U.S. PATENT DOCUMENTS

| | | | | |
|---|---|---|---|---|
| 4,141,351 A | * | 2/1979 | James et al. ............ 600/522 X |
| 4,419,998 A | * | 12/1983 | Heath ..................... 607/142 X |
| 4,494,552 A | * | 1/1985 | Heath ......................... 600/509 |
| 4,785,812 A | * | 11/1988 | Pihl et al. ...................... 607/8 |
| 4,834,103 A | * | 5/1989 | Heath ..................... 607/152 X |
| 4,964,407 A | * | 10/1990 | Baker, Jr. et al. .............. 607/27 |
| 5,441,520 A | * | 8/1995 | Olsen et al. ............ 607/119 X |
| 5,593,427 A | | 1/1997 | Gliner et al. |
| 5,607,454 A | | 3/1997 | Cameron et al. |
| 5,713,927 A | * | 2/1998 | Hampele et al. ................ 607/5 |
| 5,735,879 A | | 4/1998 | Gliner et al. |
| 5,836,993 A | | 11/1998 | Cole |
| 5,879,374 A | | 3/1999 | Powers et al. |
| 5,951,598 A | * | 9/1999 | Bishay et al. ................ 607/142 |
| 6,101,413 A | | 8/2000 | Olson et al. .................... 607/5 |
| 6,125,298 A | | 9/2000 | Olson et al. .................... 607/5 |
| 6,427,083 B1 | * | 7/2002 | Owen et al. .................... 607/5 |

FOREIGN PATENT DOCUMENTS

WO    WO 94/27674    12/1994

\* cited by examiner

*Primary Examiner*—John Rivell

(57) ABSTRACT

A system for identifying electrodes connected to a defibrillator. At least two electrodes with at least one connecting pin operatively connected to each electrode. Each connecting pin includes at least one pair of contacts. A receptacle receives each connecting pin. Circuitry is operatively connected to the receptacle for detecting shorting of the contacts to determine a type of electrode connected to the receptacle.

21 Claims, 5 Drawing Sheets

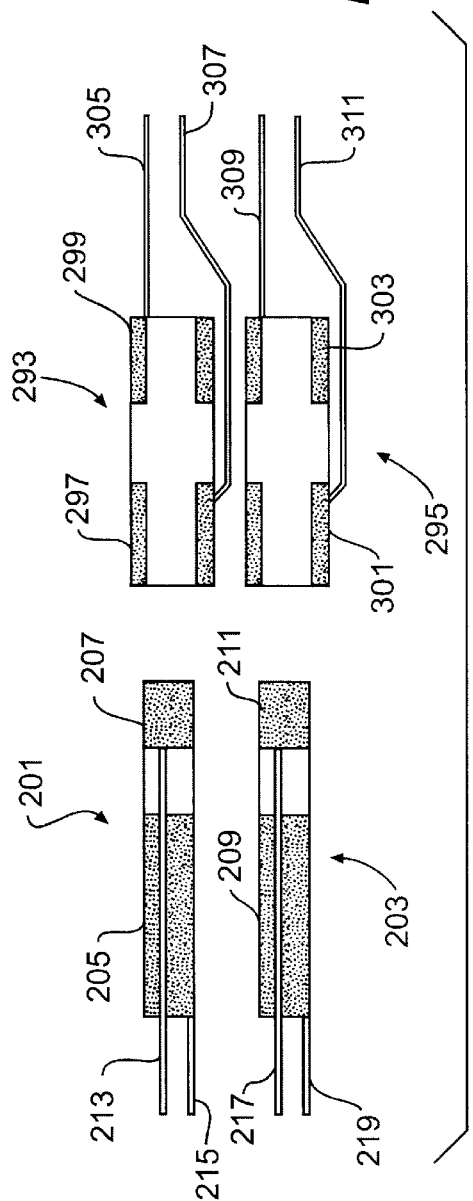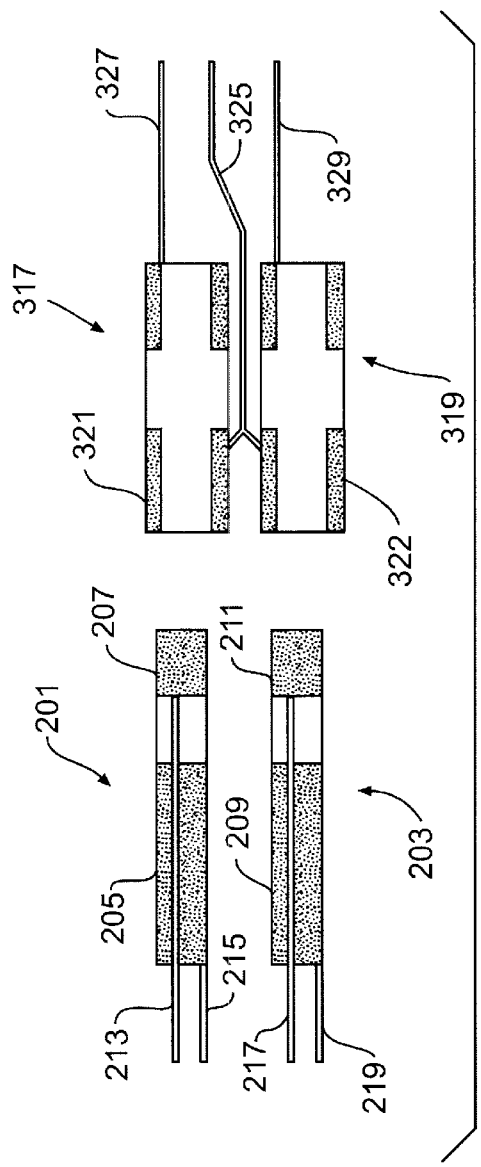

FOUR CONTACT IDENTIFICATION DEFIBRILLATOR ELECTRODE SYSTEM

BACKGROUND OF THE INVENTION

1. Field of the Invention

The invention relates to defibrillators and, in particular, to a system for permitting the type of electrode connected to the defibrillator to be determined to help ensure that the therapy applied through the defibrillator is appropriate for the type of electrode connected to the patient. The invention also relates to defibrillators and, in particular, to a system for measuring the quality of electrodes prior to being used on a patient.

2. Description of the Prior Art

Sudden cardiac death is the leading cause of death in the United States. Most sudden cardiac death is caused by ventricular fibrillation ("VF"), in which the heart's muscle fibers contract without coordination, thereby interrupting normal blood flow to the body. The only known effective treatment for VF is electrical defibrillation, in which an electrical pulse is applied to a patient's heart. The electrical shock clears the heart of the abnormal electrical activity (in a process called "defibrillation") by depolarizing a critical mass of myocardial cells to allow spontaneous organized myocardial depolarization to resume.

The electrical pulse must be delivered within a short time after onset of VF in order for the patient to have any reasonable chance of survival. To be effective, the defibrillation shock must be delivered to the patient within minutes of the onset of VF. Studies have shown that defibrillation shocks delivered within one minute after the onset of VF achieve up to a 100% survival rate. However, the survival rate falls to approximately 30% after only 6 minutes. Beyond 12 minutes, the survival rate approaches zero. Importantly, the more time that passes, the longer the brain is deprived of oxygen and the more likely that brain damage will result. Electrical fibrillation may also be used to treat shockable ventricular tachycardia ("VT"). Accordingly, defibrillation is the appropriate therapy for any shockable rhythm, that is, VF or shockable VT.

One way of providing electrical defibrillation uses implantable defibrillators, which are surgically implanted in patients that have a high likelihood of experiencing VF. Implanted defibrillators typically monitor the patient's heart activity and automatically supply the requisite electrical defibrillation pulses to terminate VF. Implantable defibrillators are expensive, and are used in only a small fraction of the total population at risk for sudden cardiac death.

External defibrillators send electrical pulses to a patient's heart through electrodes applied to the patient's torso. External defibrillators are typically located and used in hospital emergency rooms, operating rooms, and emergency medical vehicles. Of the wide variety of external defibrillators currently available, automatic and semi-automatic external defibrillators, collectively referred to as "AEDs", are becoming increasingly popular because relatively inexperienced personnel can use them. U.S. Pat. No. 5,607,454 to Cameron et al., entitled Electrotherapy Method and Apparatus, and PCT publication number WO 94/27674, entitled Defibrillator With Self-Test Features, the specifications of which are hereby incorporated by reference, describe AEDs.

AEDs provide a number of advantages, including the availability of external defibrillation at locations where external defibrillation is not regularly expected, and is likely to be performed quite infrequently, such as in residences, public buildings, businesses, personal vehicles, public transportation vehicles, among other locations. Although operators of AEDs can expect to use an AED only very occasionally, they must nevertheless perform quickly and accurately when called upon. For this reason, AEDs automate many of the steps associated with operating external defibrillation equipment. Along these lines, the operation of AEDs is intended to be simple and intuitive. AEDs are designed to minimize the number of operator decisions required.

SUMMARY OF THE INVENTION

Although AEDs were first contemplated to be used for treating adult VF and shockable VT, the present invention provides a solution that can permit AEDs to be utilized to treat pediatric patients. In order to minimize cost and simplify their use, AEDs often include only one connector for connecting electrodes. There are situations where the operator would like to use the AED as a low cost ECG monitor. The present invention can provide a means to connect and detect monitoring electrodes through the same connector used for defibrillation electrodes. The present invention can also provide the ability to monitor the condition of each electrode individually in a sealed package while connected to a defibrillator. The present invention can, therefore, permit the condition of an electrode to be monitored when each electrode is sealed in its a package.

To provide these and other advantages, the present invention provides a system for identifying electrodes connected to a defibrillator. The system includes at least one connecting pin operatively connected to an electrode. Each connecting pin includes at least one pair of contacts. A receptacle receives each connecting pin. Circuitry is operatively connected to the receptacle for detecting shorting of the contacts to determine a type of electrode connected to the receptacle.

The present invention also provides a method for determining a type of electrode attached to a defibrillator. According to the method, connecting pins operatively connected to the electrodes are inserted into a receptacle for receiving the connecting pins. It is determined whether any shorts exist between contacts on the pins and a pattern of shorts to determine the electrode type.

Still other objects and advantages of the present invention will become readily apparent by those skilled in the art from a review of the following detailed description. The detailed description shows and describes preferred embodiments of the invention, simply by way of illustration of the best mode contemplated of carrying out the present invention. As will be realized, the invention is capable of other and different embodiments and its several details are capable of modifications in various obvious respects, without departing from the invention. Accordingly, the drawings and description are illustrative in nature and not restrictive.

BRIEF DESCRIPTION OF THE DRAWINGS

Objects and advantages of the present invention will be more clearly understood when considered along with the accompanying drawings, in which:

FIGS. 3–7 represent cross-sectional views of various exemplary embodiments of both male and female portions of electrode connectors according to the present invention.

DESCRIPTION OF THE PREFERRED EMBODIMENTS

Figure 1:
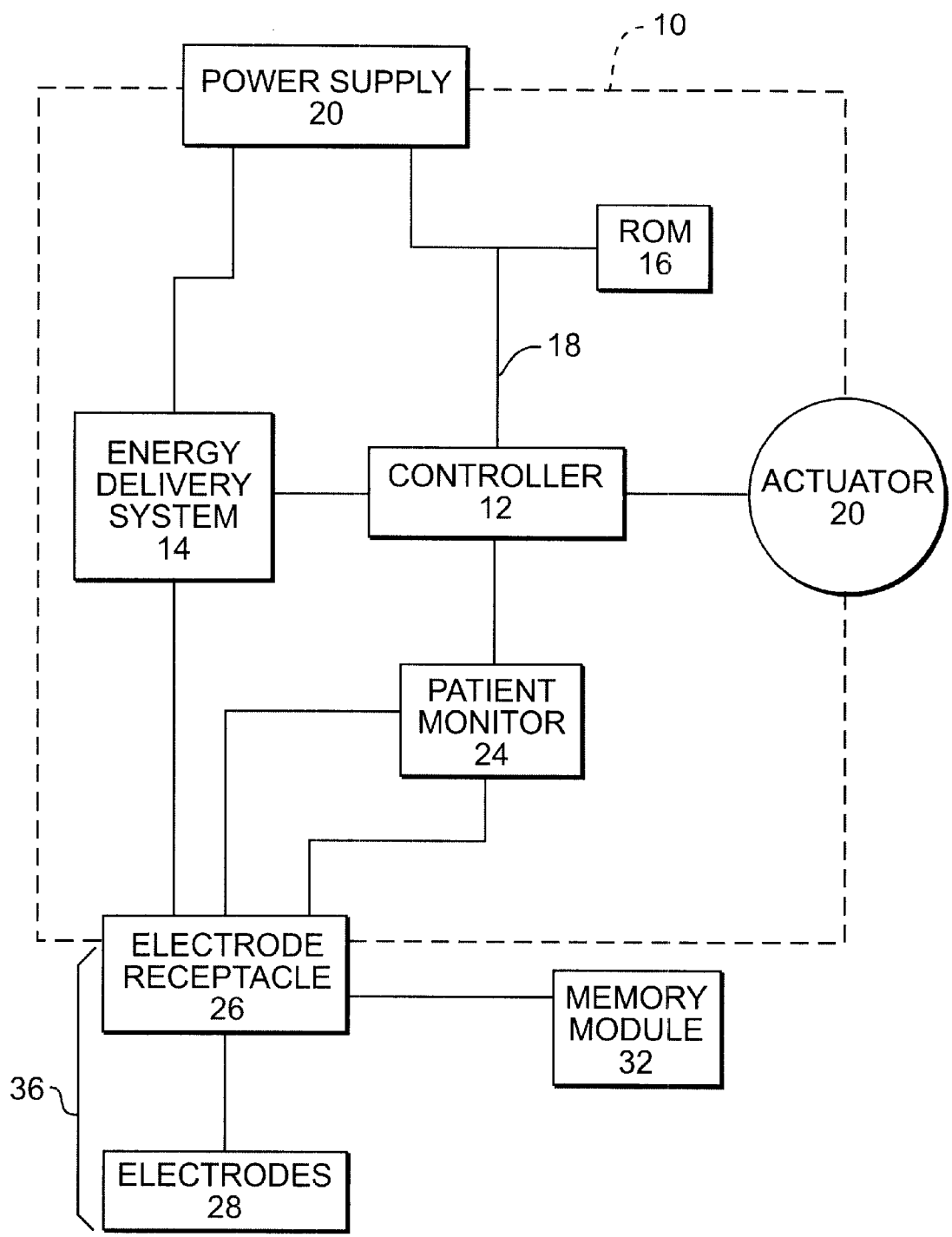
FIG. 1 represents a block diagram that illustrates elements of an embodiment of an electrotherapy device.

The treatment scheme for pediatric patients differs from that of adult patients. For example, the optimal energy required for defibrillating infants and children might differ from the energy necessary for treating adults. According to one treatment regimen, the treatment energy is 2 J/kg. Additionally, the criteria utilized for analyzing adult VF is not necessarily be appropriate for pediatric VF because of physiological differences between adults and pediatric patients. Such differences include, for example, heart rate. Additionally, the protocol recommended for treating a pediatric victim of sudden cardiac arrest differs from the protocol recommended for treating an adult, largely because pediatric VF is typically associated with respiratory failure.

The use of AEDs for pediatric patients generally has not been considered, primarily because of concerns with potential operator confusion and machine complexity. When defibrillating pediatric patients, the operator must know the appropriate energy dose to deliver, which is based at least in part on the pediatric patient's weight or age. In practical terms, this means that an AED must have the necessary circuitry to accurately produce at least two energy levels (adult and child).

AEDs provide a number of advantages, including the availability of external defibrillation at locations where external defibrillation is not regularly expected, such as public buildings, businesses, personal vehicles, and public transportation vehicles, such as airplanes, among other locations. With this widespread availability of defibrillators comes a secondary use model. Provided that it does not add significant cost or complexity, it is sometimes desirable to monitor the heart rhythm of the patient while they are conscious. Monitoring electrodes are much smaller, easier to apply, cheaper, and may be located on the patient without requiring removal of clothes. Monitoring electrodes require three electrodes to reduce common mode noise caused by the higher resistance of the smaller electrode size. Some patients may not need defibrillation or defibrillation is not formally permitted because the patient is not suffering SCA and does not meet the indications for use of an AED. Some or all AEDs could be used to monitor patients' ECG using monitoring electrodes. To do so, the AED would need to distinguish between monitoring electrodes and defibrillating electrodes. This may also necessitate providing at least three electrode contacts. Accordingly, if monitoring electrodes are being utilized, it will need to be ensured that a defibrillating shock is not delivered to a patient when only monitoring is desired. In addition, the information provided to the operator either on the display of the defibrillator or through voice prompts generated by the defibrillator can be specifically tailored to the monitoring function that the AED is being used for.

To ensure that an AED produces the appropriate voltage for an adult or a pediatric patient, the AED must provide means for choosing the proper energy level. Also, to ensure that a defibrillating shock is not delivered when monitoring is desired, regardless of the type of patient, the AED must be able provide means for selecting a monitoring electrode function. The present invention provides a system that can accomplish both of these objectives.

By knowing the type of patient, an AED can properly analyze VF. The AED can manually or automatically be informed of the type of patient. The present invention can prevent application of an incorrect defibrillating voltage to a patient when it is desired to monitor a patient. By doing so, the present invention can simplify the treatment of a patient and reduce uncertainty in treatment by eliminating decision making by the operator. Reduction of complexity and decision making by the operator is important in the context of AEDs since the operators typically are lay people without training and whose primary occupation is not life saving, such as police officers and flight attendants.

Use of AEDs by untrained or minimally trained operators for a patient in SCA is a very stressful and time critical operation. Minimization of the number of steps required to defibrillate and improving the reliability of defibrillation are key aspects of an AED design. Electrodes that are sealed with a connector inside an enclosure, such as a bag, can require multiple steps by the operator. First, a user must open the sealed bag. Second, the operator must plug the electrodes into the AED. Third and fourth, the operator must remove a release liner, which typically covers a gel on the electrode pads from an electrode and place the electrode on the patient. Fifth and sixth, the operator must remove the release liner from the second electrode and place electrode on the patient. One way to minimize steps that an operator must perform is to have the defibrillation electrodes already connected to the AED prior to the time when the AED is needed. This eliminates the second step in the above-described process.

In addition, the electrodes may be designed such that each electrode is individually sealed in its own pouch. Electrodes that are individually sealed and preconnected are disclosed in co-pending U.S. patent application Ser. No. 09/145,168, to Bishay et al., filed Sep. 1, 1998, for *Independently Deployable Sealed Defibrillator Electrode Pad And Method Of Use,* and assigned to the same assignee as the present application, the entire contents of the disclosure of which are hereby incorporated by reference. In the case of individually sealed and preconnected electrodes, the act of opening the sealed electrode and removing the release liner can be one simple operation. This eliminates the first step of the above-described process. One advantage of electrodes that are preconnected to an AED is the ability to automatically test and verify the AED functionality with the electrodes included prior to use. Known methods and systems for testing preconnected electrodes typically do not allow for electrodes that are individually sealed. The present invention can provide a means to electrically test the electrodes or any other style of preconnected electrodes while connected to an AED prior to use.

The following description provides general background of an AED to facilitate understanding of the present invention. The AED described herein provides just one example of an AED that the system and method according to the present invention may be utilized with. FIG. 1 is a block diagram showing a device 10. Device 10 is an electrotherapy device. The device 10 may include the ability to defibrillate, cardiovert, or pace a patient, or a combination of these features. Device 10 has a controller 12 that operates an energy delivery system 14 and performs other aspects of the operation of the device. Software instructions for the operation of the device are accessible from read only memory (ROM), such as incorporated ROM 16. The controller accesses instructions for operation from ROM 16. It should be understood that, in this and other embodiments described below, "controller" means a microprocessor, controller, gate array, other control logic, or any combination of these elements.

Controller 12 communicates with ROM 16 via a memory bus 18. A recordable memory module 32 is attached to device 10 via an electrode system 36, as shown in FIG. 1. Electrode system 36 includes electrodes 28 and an electrode adapter 26.

Electrode receptacle 26 is connected to electrodes 28. Electrodes are removably connected to the device 10. A suitable electrode system 36 adaptable for use in this invention would be, for example, Heartstream ForeRunner® electrodes.

Electrodes 28 communicate with a patient monitor 24 via electrode receptacle 26 to provide patient ECG data from the patient to the patient monitor 24. Electrodes include electrodes capable of delivering defibrillation, monitoring a patient condition, delivering pacing pulses, or a combination of those features. In an AED, the patient monitor 24 monitors the patient for a heart rhythm and subsequently determines whether the monitored rhythm is shockable. When the rhythm is shockable, the patient monitor 24 then communicates a shock decision to the controller 12. The controller 12, then communicates to the energy delivery system 14. The energy delivery system 14 then delivers a therapeutic energy pulse to the patient (not shown) through electrodes 28 attached to the defibrillator 10 via electrode receptacle 26, using the power supply 20 as the energy source.

The power supply may include elements such as batteries, a DC and/or an AC power source. The DC power source could be batteries. The power supply could also include a DC—DC and/or AC to DC converters. Additionally, the power supply could include a high voltage charge circuit. Furthermore, the power supply could include an energy storage capacitor.

Figure 2:
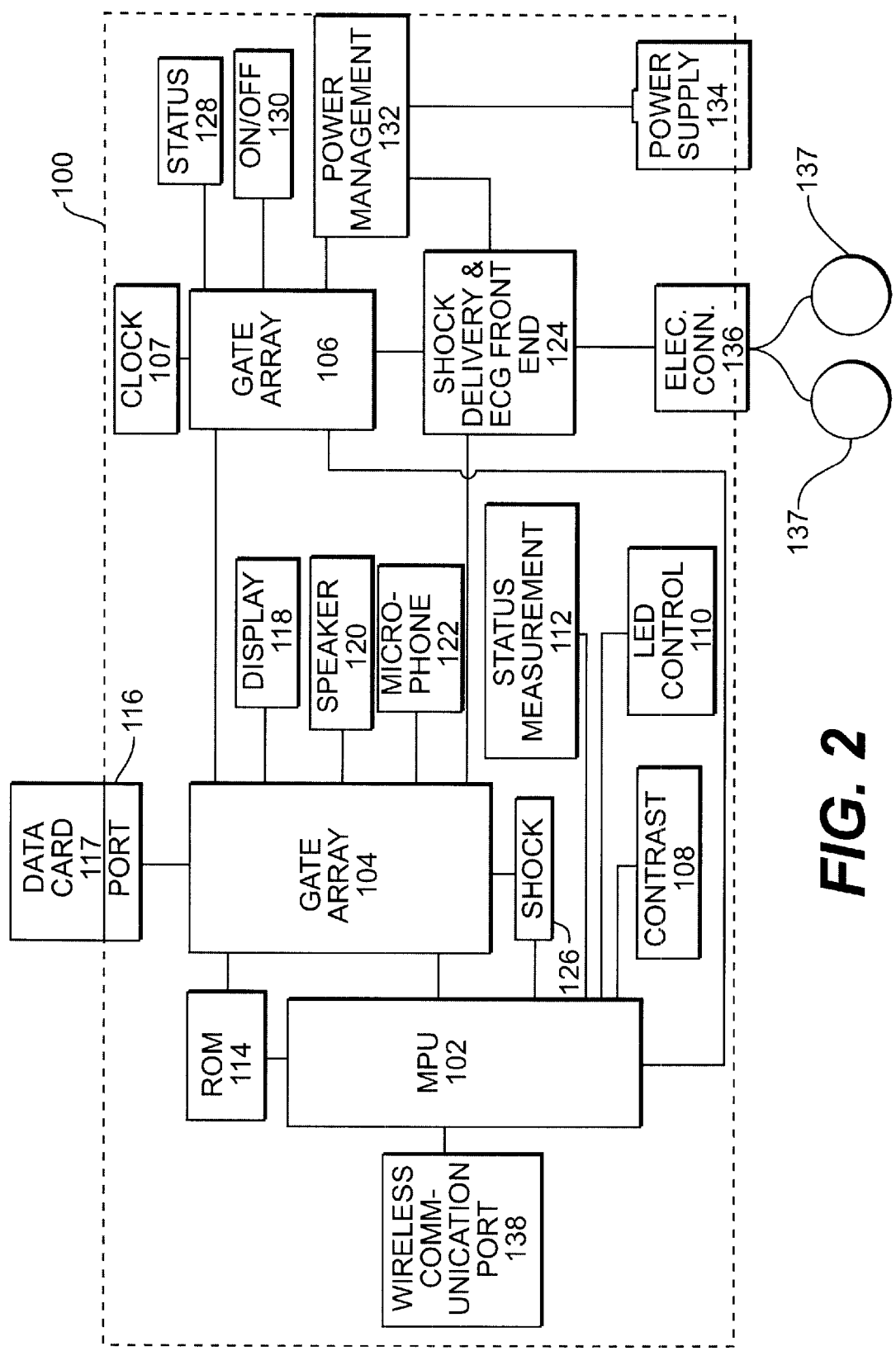
FIG. 2 represents a block diagram that illustrates major components of an automatic external defibrillator.

The major components of an AED are shown in FIG. 2 in block diagram form. Further detailed information about the operation of an AED can be obtained in U.S. Pat. No. 5,836,993, to Cole, for "Electrotherapy Device Control System and Method", and U.S. Pat. No. 5,593,427 to Gliner et al., for "Electrotherapy Method," the specifications of both of which are incorporated herein by reference. As will be appreciated by those of skill in the art, the invention can be used in a variety of AEDs and is not limited to this configuration, which is used for illustration purposes only.

In this illustration, defibrillator control functions are divided among a microprocessor unit (MPU) 102 and two custom gate arrays 104 and 106.

MPU 102 performs program steps according to software instructions provided to it from ROM 114. MPU 102 controls the operation of certain buttons (such as display contrast buttons 108) and certain system LED's 110 (such as LED's associated with the shock button and the electrode connector). MPU 102 also receives system status information as shown by block 112.

Gate array 104 implements the memory map to system ROM 114. System ROM 114 is preferably flash ROM, although EPROM or any other electrically erasable and programmable nonvolatile memory could be used. Gate array 104 also controls a display 118, a speaker 120, and a microphone 122. Gate array 104 can actuate a relay within the shock delivery and ECG front-end system 124 in response to actuation of a shock button 126 by a user during treatment mode.

Gate array 106 provides a system monitor function by performing automatic self-tests of the defibrillator and its components. The gate array 106 displays the operational status of the defibrillator on a status display 128. Details of suitable self-tests may be found in U.S. Pat. No. 5,879,374, to Powers et al., for "External Defibrillator with Automated Self-Testing Prior to Use," the specification of which is incorporated herein by reference. Gate array 106 is also the defibrillator's interface with a user-activated on/off switch 130. Gate array 106 controls the power management subsystem 132 to provide power to operate system components from power supply 134 and to provide energy to the shock delivery system's capacitor(s) for a therapeutic shock during treatment mode. Gate array 106 also interfaces with the defibrillator's ECG front end, enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in U.S. Pat. No. 5,735,879 to Gliner et al., for "Electrotherapy Method for External Defibrillators"; and U.S. Pat. No. 5,607,454, to Cameron et al. for "Electrotherapy Method and Apparatus"; the specifications of both of which are incorporated herein by reference.

The MPU can send and receive data and operational commands via the wireless communication port 138. This is used to assist manufacturing and to communicate status and use data to external devices. In addition, the port 138 permits remote operation of certain device features such as requesting and receiving device status.

These defibrillator components communicate with each other over suitable communication buses, as shown.

External defibrillator 100 can be operated in different modes, such as self-test mode, stand-by mode, set-up mode, patient treatment mode, training mode and code-transfer mode. The operational characteristics of defibrillator 100 differ in each mode. In addition, the operational characteristics of the defibrillator in any one of the modes can be changed as explained below.

Operation of the external defibrillator of this embodiment commences with the insertion of a power supply 134 or user activation of the power on button. Once gate array 106 confirms that a power supply 134 is inserted, gate array 104 prompts MPU 102 to begin its boot sequence. The boot sequence begins with MPU 102 sending out a series of addresses to ROM 114.

As is known in the art, while in patient treatment mode, the defibrillator 100 typically (1) determines whether electrodes 137 are attached to electrode connector 136; (2) receives patient impedance and/or ECG information from a patient through such electrodes; (3) analyzes the patient contact information to determine whether a patient is connected; (4) analyzes the ECG information to determine whether a therapeutic shock is advised; and (5) delivers a shock to the patient through the electrodes 137 if a shock is advised and if the shock button 126 is actuated by a user.

As described above, the present invention may be utilized with an AED in treating adults, pediatric patients, and monitoring all patients. To facilitate differentiation of adult defibrillating electrodes, pediatric defibrillating electrodes, and monitoring electrodes, the present invention provides a system that can identify the type of electrodes attached to the defibrillator. If the system can identify the type of electrode, the system can then provide the appropriate treatment or monitoring. Along these lines, the present invention can permit automatic instructions in an AED to be adapted to particular circumstances.

An embodiment of a system according to the present invention can include at least two electrodes. The number of electrodes may depend upon whether the electrodes are utilized for treatment or monitoring. At least one connecting pin is operatively connected to each electrode. The pins may be interconnected in a single structure. However, the pins still provide individual electrically isolated connections between the AED and the electrodes.

Each pin includes at least pair of contacts. Such contacts may be similar to contacts included in headphone systems. In such systems, a single connecting pin can include two or more electrical contacts. Each contact may be separated from the others by an electrical insulator. This arrangement of contacts is easily visible in such connecting pins by the arrangement of a black band in the pins. The connecting pins can include a central interior contact surrounded by a cylindrical exterior contact. The black band is the visible portion of an insulator that extends entirely between the two contacts. A connecting pin according to the present invention may include more than two contacts. A system that includes two electrodes that each include two contacts would provide four electrical contacts.

According to the present invention, a short or absence of a short between one or more of the contacts of one or more connecting pins determines the identification of the type of electrode. A receptacle receives the connecting pins. Circuitry operatively connected to the receptacle detects the pattern of shorts on each contact and between and among contacts to determine the type of electrode attached to an AED. The appropriate therapy may then be carried out through the electrodes even if the therapy includes monitoring.

In a system that includes two connecting pins each having two contacts, a contact of a first may be shorted to a contact of a pin of a second electrode. Alternatively, the contacts on a first pin may be shorted to each other, while no contact on a second pin may be shorted. Furthermore, the contacts on both pins may be shorted to each other.

Typically, the types of electrodes attached to an AED include adult defibrillating electrodes, pediatric defibrillating electrodes, and monitoring electrodes. Any pattern of contact may correspond to any particular type of electrode. The AED may be programmed to correlate the pattern of shorts with the type of electrode and type of therapy. According to one example, adult electrodes each include a connecting pin that includes a pair of shorted contacts.

Pediatric defibrillating electrodes may be attenuated or non-attenuated. According to one embodiment, attenuated pediatric electrodes each include a connecting pin that includes a pair of contacts. The pair of contacts in only one of the connecting pins is shorted. In this way, an AED can distinguish pediatric defibrillating electrodes from adult defibrillating electrodes.

By incorporating the electrodes in a polarized connector, much like an electrical plug that includes one prong larger than the other, the present invention can distinguish among other types of electrodes. Along these lines, to differentiate between attenuated and non-attenuated pediatric defibrillating electrodes, non-attenuated pediatric defibrillating electrodes may also each include a connecting pin that includes a pair of contacts. The pair of electrodes in only one of the connecting pins is shorted. However, the arrangement of the pins having the shorted and non-shorted contacts is opposite that for attenuated pediatric defibrillating electrodes.

Once it is determined that pediatric electrodes are connected, the therapy may be tailored accordingly. Along these lines, the therapy may be carried out according to the description in U.S. Pat. No. 6,134,468, issued Oct. 17, 2000, to Morgan et al., for Method and Apparatus for Reducing Defibrillation Energy, the entire contents of the disclosure of which are hereby incorporated by reference.

FIGS. 3–7 illustrate various embodiments of the present invention that may be utilized for different types of electrodes. The left-hand side of each of FIGS. 3–7 shows an embodiment of male connecting pins 201 and 203 that may be utilized with each of the embodiments of female receptacles shown in the right-hand side of the figures. The embodiment of the male connecting pins shown in FIGS. 3–7 can provide a defibrillator receptacle connection to a patient monitor and energy delivery circuitry. Each male connecting pin shown in FIGS. 3–7 includes two contacts 205, 207, 209, and 211. A lead wire 213, 215, 217, and 219 is attached to each contact. The four wires may be monitored by the patient monitor for determining one or more shorts between pins and for measuring patient data such as ECG and Electrode Patient Contact Impedance. The energy delivery circuitry may be connected to the four wires through switches that may be engaged only during energy delivery. During energy delivery, lead wires 213 and 215 and/or lead wires 217 and 219 may be shorted together. The delivered energy may be applied through lead wire 213 in common with lead wire 215 through the electrodes and patient and returning through lead wire 217 in common with lead wire 219.

Figure 3:
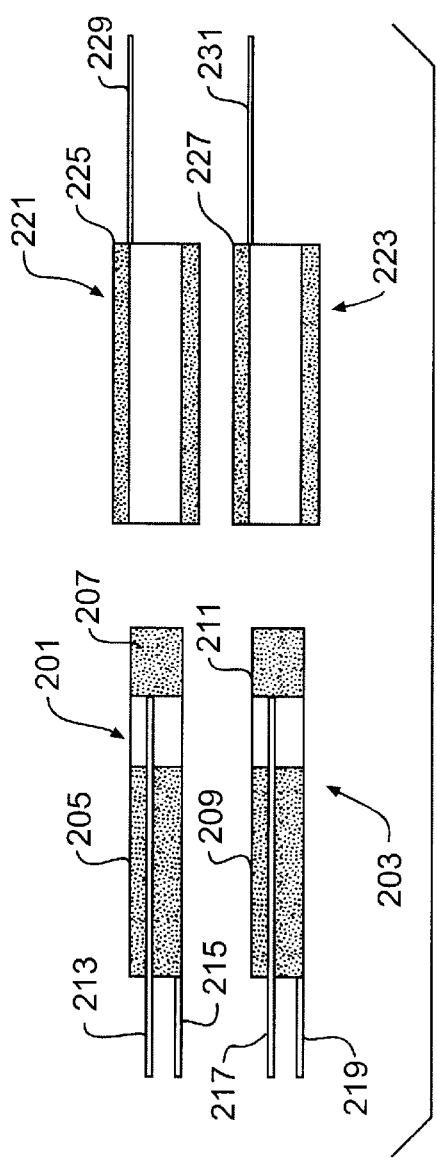

FIG. 3 illustrates an embodiment of the present invention that may be utilized for adult defibrillating electrodes. The right-hand side of FIG. 3 represents the electrode connector including a pair of receptacles 221 and 223 for receiving the connecting pins. Each receptacle of this embodiment includes a contact 225 and 227 with a lead wire 229 and 231 extending therefrom. Lead wire 229 may be connected to one electrode. Also, lead wire 231 may be connected another electrode. As can be seen in FIG. 3, when the connecting pins are inserted into the receptacles, the contacts on each connecting pin will be shorted. Detection of these shorts can permit the identification of the type of electrode, in this case, standard adult defibrillating electrodes.

Figure 4:
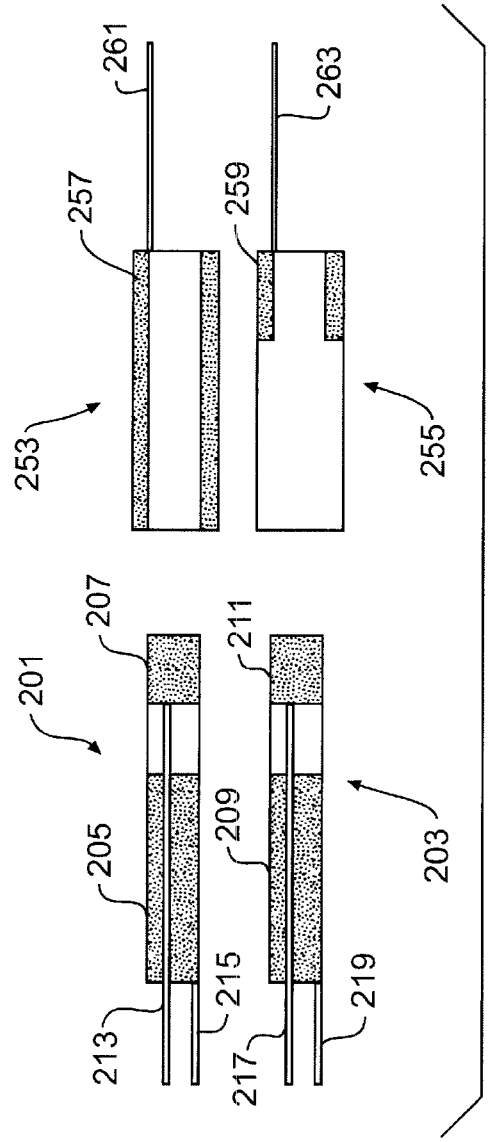

FIG. 4 illustrates an embodiment of the present invention that may be utilized for non-attenuated pediatric defibrillating electrodes. The right-hand side of FIG. 4 represents the electrode connector containing a pair of receptacles 253 and 255 for receiving the connecting pins. Each receptacle of this embodiment includes a contact 257 and 259 with a lead wire 261 and 263, respectively, extending therefrom. Lead wire 261 may be connected to one electrode and lead wire 263 connected to another electrode. Contact 257 extends the entire length of the receptacle. On the other hand, contact 259 only has a length that will permit the contact to engage the contact on the tip of the pin 235. Therefore, in the embodiment shown in FIG. 4, when the connecting pins are inserted into the receptacles, the contacts on only the connecting pin 233 will be shorted. Detection of this short can permit the identification of the type of electrode, in this case, non-attenuated pediatric electrodes.

Figure 5:
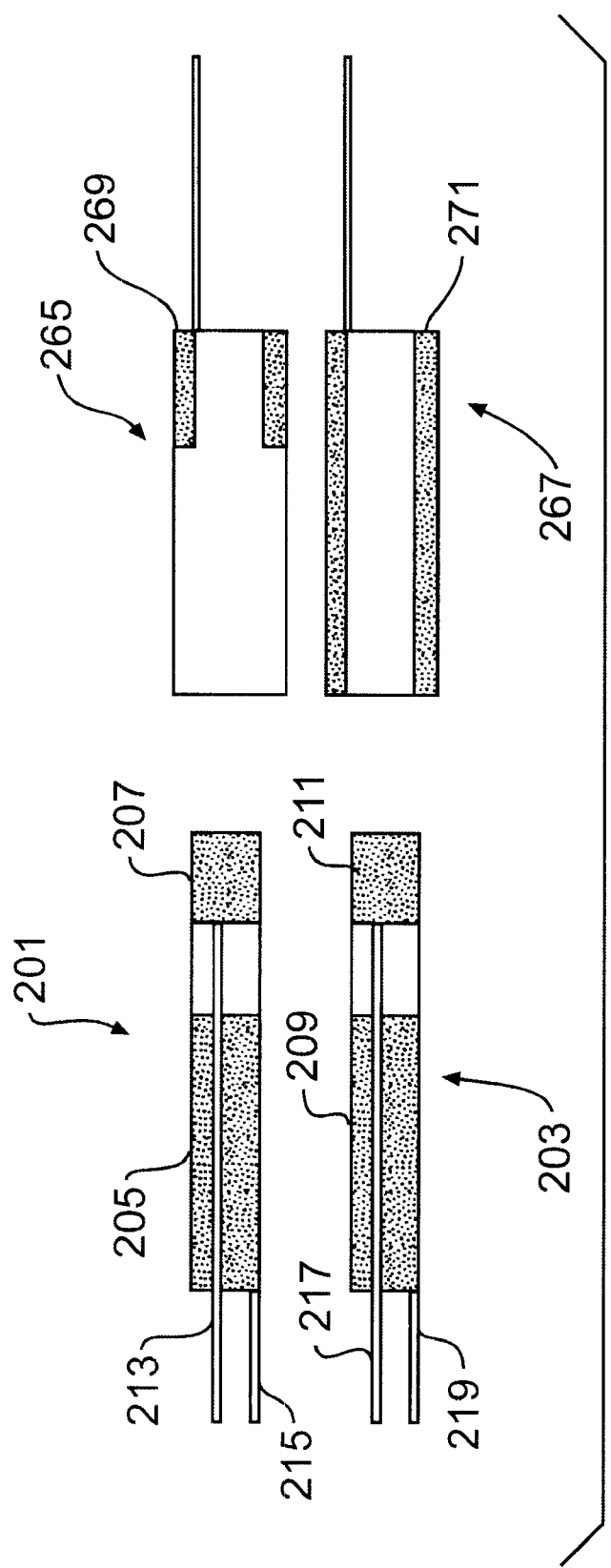

FIG. 5 represents an embodiment similar to that shown in FIG. 4. However, the receptacles 265 and 267 in the embodiment illustrated in FIG. 5 have contacts 269 and 271 that result in contacts on the opposite connecting pin being shorted as compared to the embodiment shown in FIG. 4. The embodiment shown in FIG. 5 could be utilized for attenuated pediatric electrodes.

The embodiments shown in FIGS. 4 and 5, or any of the other figures, may be utilized where the connecting pins and receptacles are brought together in a manner similar to a polarized electric plug, where one of the prongs of the plug is larger than the other. In this manner, the pattern of shorts could be used to differentiate between electrode types. Of course, what type of electrodes are associated with what type of connector may vary and the associations described herein are only examples.

FIG. 6 illustrates an embodiment of connecting pins and receptacles according to the present invention that may be utilized for pre-connected electrode connectors. The right-hand side of FIG. 6 illustrates an electrode connector that includes receptacles 293 and 295 for receiving the connecting pins shown in the left-hand side of FIG. 6. Each receptacle includes a pair of contacts 297, 299, 301, and 303. Lead wires 305, 307, 309, and 311 extend from the contacts. Lead wires 305 and 307 may be connected to one electrode containing two foil plates covered by a layer of gel. Lead wire 305 may be connected to one foil plate and lead wire 307 connected to another. Lead wires 39 and 311 connect to the other electrode in a similar fashion. When the male connecting pins are inserted into the receptacles, none of the contacts will be shorted. However, each electrode will present a resistance between the contacts due to the gel that spans between the two foil plates of each electrode. The pre-connected electrodes may be detected by the measurement of the gel resistance between the two contacts of each electrode. The level of resistance measured may be utilized to determine the quality of the gel so that the user may be alerted to the need for replacing the electrodes.

As also described herein, the present invention can provide a connecting pin and receptacle arrangement for use as a 3-wire ECG electrode connector. FIG. 7 illustrates such an embodiment of the present invention.

The right-hand side of FIG. 7 illustrates an embodiment of a monitoring electrode connector that includes a pair of receptacles 317 and 319 similar to the receptacles shown in FIG. 6. However, two of the contacts 321 and 323 in the embodiment shown in FIG. 7 are shorted by the connection with lead wire 325. Each of lead wires 325, 327, and 329 can terminate with a snap connector that can be connected to standard disposable ECG monitoring electrodes. This short will not occur unless the connecting pins are fully engaged and will help to prevent inadvertent discharge with a direct short across the defibrillation pins.

The present invention can also permit determination of whether the connecting pins are fully inserted into the receptacles. According to one embodiment, the contacts may be designed such that the contacts that provide identification information by a short are the last contacts to connect as the connector is inserted. These contacts may also be designed so that there are no false indications of shorts between contacts during the insertion process. Once this short between contacts is detected, then the contacts used for delivering therapy or measuring ECG can be assured to be fully in contact.

Monitoring electrodes would have a different arrangement of contacts to permit differentiation from other types of electrodes. According to one embodiment, three monitoring electrodes are utilized. Two of the three monitoring electrodes are operatively connected to the two contacts that are for the ECG input. The remaining two contacts are shorted together and connected to the third monitoring electrode to become the reference electrode sometime referred to as the driven electrode. This is also the case with active feedback for improved common mode noise reduction. This short will not occur unless the electrodes are fully engaged in the receptacle. When an AED detects this arrangement, the AED will know that monitoring electrodes are attached to the AED. Such an arrangement can provide an extra margin of safety to inadvertent discharge with a direct short across the defibrillation pins.

In some cases, the electrodes may be preconnected to an AED. The incidence for pediatric defibrillation is relatively small in comparison to adult defibrillation. Therefore, it makes sense to design preconnected electrodes to be adult only electrodes. The adult preconnected electrodes would include a connecting pin with none of the contacts shorted. This will provide two contacts for each electrode. The AED circuitry used to detect shorts between contacts will measure the resistance between the contacts of each pin that results from the conductive hydrogel of the preconnected electrodes. An impedance within a certain range will differentiate the preconnected adult electrodes from all other electrodes.

In an embodiment where the electrodes are preconnected, each electrode may include a pair of electrically isolated metal foil members. A connection will be made to each foil member. The conductive gel, typically a hydrogel, required to make good contact with a patient's skin will overlie each foil member. The two foil members and the connection to each foil member will permit the defibrillator to test the impedance of the conductive gel of each electrode separately in the packaged state if contact may be made to the electrodes as packaged. If the moisture level of the gel does not fall within a particular range, the gel may not function properly as discussed below in greater detail. During defibrillation, both wires attached to the two foil pieces of an electrode will by driven at the same potential to permit them to function as a single electrode.

Water loss can affect the mechanical properties of the hydrogel as well. In most hydrogels, the loss of water causes the hydrogel to skin over or solidity, especially around the edges, which destroys the ability of the hydrogel to adhere to the skin. This partial or complete loss of adhesion can render an electrode useless since it cannot then create or maintain an effective contact with the skin. Thus, the drying of the electrode pad can prevent or attenuate receipt of electrocardiogram (ECG) signals by a defibrillator. As a result, the drying of the electrode pad can alter the delivery of defibrillation energy delivered to the patient.

Additionally, poor or uneven contact of the electrode pad with a patient's skin may unduly concentrate energy transfer during defibrillation into areas that exhibit good skin contact. Higher than usual current densities that result from poor or uneven skin contact can cause skin burns. If the current is not delivered to a patient in the manner that an electrode pad was designed for, the resulting treatment delivered to the patient may be altered, compromising patient survivability.

Among the advantages of the present invention are that it is compatible with existing electrode systems. The present invention also has the ability to detect whether a user has fully plugged an electrode connector into a receptacle. In an embodiment that includes two connecting pins each including two contacts, by manipulating the contacts and shorts on the pins and between contacts, the present invention can differentiate among as many as five different electrode types. The present invention also provides a failsafe three wire ECG monitoring solution that is detectable and prevents inadvertent shock. As described above, the present invention additionally has the ability to identify and test a preconnected electrode system.

Furthermore, the present invention provides improved monitoring of impedance with a split electrode. A four-wire impedance measurement will significantly reduce artifacts generated at the skin-electrode interface. By providing a split electrode system, the present invention also has the ability to detect and measure the quality of electrode placement by measuring the impedance between two halves of the split electrode. Additionally, the present invention provides improved ECG monitoring with a split electrode.

The present invention as described above includes examples of contacts and shorting patterns associated with certain types of electrodes. Naturally, any pattern of contacts and shorting may be included that permits the present invention to distinguish among electrode types and thereby permit application of the appropriate therapy. Additionally, the connecting pins may include more than two contacts. Additionally, the type of the contacts such as male or female can exist at either the AED or the electrodes The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed:

1. A system for identifying electrodes connected to a defibrillator, the system comprising:
   at least one connecting pin operatively connected to an electrode, each connecting pin comprising at least one pair of contacts;
   a receptacle for receiving each connecting pin; and
   circuitry operatively connected to the receptacle for detecting shorting of the contacts to determine a type of electrode connected to the receptacle.

2. The system according to claim 1, wherein the at least two electrodes comprise one of adult defibrillation electrodes, attenuated pediatric defibrillation electrodes, non-attenuated pediatric defibrillation electrodes, and monitoring electrodes.

3. The system according to claim 2, wherein the system comprises a pair of adult defibrillation electrodes each comprising a connecting pin including a pair of shorted contacts.

4. The system according to claim 2, wherein the system comprises a pair of attenuated pediatric defibrillation electrodes each comprising a connecting pin including a pair of contacts, wherein only one of the pairs of contacts is shorted.

5. The system according to claim 2, wherein the system comprises a pair of non-attenuated pediatric defibrillating electrodes each comprising a connecting pin including a pair of contacts, wherein only one of the pairs of contacts is shorted.

6. The system according to claim 1, wherein the shorting of the contacts permits the circuitry to detect whether the electrodes are fully engaged in the receptacle.

7. The system according to claim 2, wherein the system comprises three monitoring electrodes and two connecting pins, a first one of the electrodes is connected to at least one contact of one of the connecting pins, a second one of the electrodes is connected to at least one contact of a second of the connecting pins, and a third one of the electrodes is connected to at least one contact of each connecting pin not connected to the other electrodes.

8. The system according to claim 1, wherein the electrodes are preconnected to the defibrillator each comprising a connecting pin including a pair of contacts that are not shorted.

9. The system according to claim 8, wherein the electrodes comprise a pair of adult defibrillation electrodes each comprising a connecting pin including a pair of contacts that are not shorted.

10. The system according to claim 1, wherein a contact of a pin of a first of the at least two electrodes is shorted to a contact of a pin of a second of the at least two electrodes.

11. The system according to claim 1, wherein the at least one pair of contacts on a first of the at least two electrodes are shorted and none of the contacts on a second of the at least two electrodes are shorted.

12. The system according to claim 1, wherein the at least one pair of contacts on both of the at least two electrodes are shorted.

13. The system according to claim 9, further comprising:
    two separate metal foil members associated with each electrode;
    an electrical connection to each foil member;
    a region of electrically conductive gel overlying the foil members;
    wherein the foil members permit the impedance of the gel to be tested while packaged.

14. A method for determining a type of electrode attached to a defibrillator, the method comprising:
    inserting connecting pins operatively connected to the electrodes into a receptacle for receiving the connecting pins; and
    detecting the presence or absence of shorts between contacts on the pins and a pattern of shorts to determine the electrode type.

15. The method according to claim 14, wherein the method determines a pattern of shorts between contacts on each connecting pin and between contacts on different connecting pins.

16. The method according to claim 14, wherein detecting the shorts permits detecting whether the contacts are fully engaged in the receptacle.

17. The method according to claim 14, wherein detection of shorts between two contacts included on each of a pair of connecting pins operatively connected to a pair of electrodes indicates that the electrodes are adult defibrillation electrodes.

18. The method according to claim 14, wherein detection of shorts between one set of two contacts included on each of a pair of connecting pins operatively connected to a pair of electrodes indicates that the electrodes are attenuated pediatric defibrillation electrodes.

19. The method according to claim 14, wherein detection of shorts between one set of two contacts included on each of a pair of connecting pins operatively connected to a pair of electrodes indicates that the electrodes are non-attenuated pediatric defibrillation electrodes.

20. The method according to claim 14, wherein detection of shorts between ring contacts included on each of a pair of connecting pins operatively connected to a pair of electrodes indicates that the electrodes are monitoring electrodes.

21. A system for identifying and testing preconnected electrodes tar a defibrillator, the system comprising:
    at least one pair of connecting pins, each connecting pin comprising a pair of contacts;
    at least one pair of receptacles for receiving each pair of connecting pins, each receptacle comprising a pair of contacts, wherein when the pins are inserted into the receptacles none of the contacts are shorted.

* * * * *